United States Patent
Si

(10) Patent No.: US 9,789,058 B2
(45) Date of Patent: Oct. 17, 2017

(54) OPHTHALMIC COMPOSITION FOR THE TREATMENT OF OCULAR INFECTION

(71) Applicant: CooperVision International Holding Company, LP, St. Michael (BB)

(72) Inventor: Erwin C. Si, Alameda, CA (US)

(73) Assignee: CooperVision International Holding Company, LP, St. Michael (BB)

( * ) Notice: Subject to any disclaimer, the term of this patent is extended or adjusted under 35 U.S.C. 154(b) by 0 days.

(21) Appl. No.: 15/314,137

(22) PCT Filed: Jun. 18, 2015

(86) PCT No.: PCT/GB2015/051790
§ 371 (c)(1),
(2) Date: Nov. 28, 2016

(87) PCT Pub. No.: WO2015/193677
PCT Pub. Date: Dec. 23, 2015

(65) Prior Publication Data
US 2017/0196805 A1   Jul. 13, 2017

Related U.S. Application Data

(60) Provisional application No. 62/014,777, filed on Jun. 20, 2014.

(51) Int. Cl.
*A61K 9/00* (2006.01)
*A61K 31/785* (2006.01)
*A61K 38/16* (2006.01)

(52) U.S. Cl.
CPC .......... *A61K 9/0048* (2013.01); *A61K 9/0051* (2013.01); *A61K 31/785* (2013.01); *A61K 38/16* (2013.01)

(58) Field of Classification Search
CPC .... A61K 9/0048; A61K 9/0051; A61K 31/16; A61K 31/765; A61K 31/785; A61K 38/02; A61K 38/16; A61L 12/14; A01N 33/04; A01N 35/08
See application file for complete search history.

(56) References Cited

U.S. PATENT DOCUMENTS

| 2005/0074467 | A1 | 4/2005 | Fujita et al. | |
| 2006/0264353 | A1* | 11/2006 | Maxey | A61K 31/557 514/310 |
| 2012/0277239 | A1* | 11/2012 | Horn | A61K 31/498 514/249 |
| 2013/0156791 | A1* | 6/2013 | Perfettini | A61K 31/7088 424/159.1 |
| 2014/0178327 | A1* | 6/2014 | Morris | A01N 33/12 424/78.04 |

FOREIGN PATENT DOCUMENTS

| CN | 101822736 A | 9/2010 |
| CN | 101954113 A | 1/2011 |
| JP | 2001-261552 A | 9/2001 |
| JP | 2002-020320 A | 1/2002 |
| JP | 2006201247 A | 8/2006 |
| WO | 2014096852 A1 | 6/2014 |
| WO | 2014192068 A1 | 12/2014 |

OTHER PUBLICATIONS

Translation of WO 2014/192068 (Dec. 4, 2014).*
International Search Report and Written Opinion issued in corresponding International Patent Application No. PCT/GB2015/051790 dated Sep. 7, 2015 (11 pages).
Zhou et al., "A photopolymerized antimicrobial hydrogel coating derived from epsilon-poly-l-lysine," Biomaterials, vol. 32, 2011, pp. 2704-2712.
Demand filed Apr. 18, 2016 in corresponding International Patent Application No. PCT/GB2015/051790 (18 pages).
Response to Written Opinion of the International Preliminary Examining Authority dated Jun. 13, 2016 and Written Opinion of the International Preliminary Examining Authority issued in corresponding International Patent Application No. PCT/GB2015/051790 dated May 24, 2016 (18 pages).
International Preliminary Report On Patentability issued in corresponding International Patent Application No. PCT/GB2015/051790 dated Oct. 20, 2016 (9 pages).
Examination Report received in corresponding United Kingdom Patent Application No. GB1621904.0 dated Jan. 26, 2017 (4 pages).
Office Action issued in corresponding Japanese Patent Application No. 2016-573491 dated May 22, 2017 with English translation (9 pages).

* cited by examiner

*Primary Examiner* — Jeffrey E Russel
(74) *Attorney, Agent, or Firm* — Kilyk & Bowersox, P.L.L.C.

(57) ABSTRACT

An ophthalmic composition for administration to an eye of a patient for the treatment of an ocular infection. The ophthalmic composition contains an ε-polylysine (εPL) in an amount effective to treat or control or prevent the ocular infection.

18 Claims, No Drawings

OPHTHALMIC COMPOSITION FOR THE TREATMENT OF OCULAR INFECTION

This application is a National Stage Application of PCT/GB2015/051790, filed Jun. 18, 2015, which claims the benefit under 35 U.S.C. §119(e) of prior U.S. Provisional Patent Application No. 62/014,777, filed Jun. 20, 2014.

FIELD

The field of the invention relates to ophthalmic compositions for the treatment or control of an ocular infection, particularly bacterial conjunctivitis caused by an antibiotic-resistant bacterium.

BACKGROUND

The emergence and spread of antimicrobial resistance among ocular pathogens has received widespread attention and raised concern among ocular health practitioners. One particular pathogen that is of special concern is methicillin-resistant *Staphylococus aureus* (MRSA). There are two types of MRSA, hospital- or healthcare-associated MRSA (HA-MRSA) and community-associated MRSA (CA-MRSA). The difference between the two lies not just on the source of the pathogen, but also in their genetic makeup. HA-MRSA is typically a multidrug-resistant organism, while CA-MRSA isolates are usually susceptible to most non-beta-lactam antimicrobial agents. The percentage of MRSA among clinical *Staphylococcus aureus* isolates was reported to be 16.8% in the United States in 2006 (Asbell et al. Am J Ophthalmol. (2008) 145:951-958). Yet in year 2007 and 2008, the percentage elevated to around 50% (Asbell et al. Ocular TRUST 3: Ongoing Longitudinal Surveillance of Antimicrobial Susceptibility in Ocular Isolates, presented at the 2009 ASCRS Symposium & Congress on Cataract, IOL, and Refractive Surgery; and the ASOA Congress on Ophthalmic Practice Management and Clinical & Surgical Staff Program). The rate is similar to those rates reported in a Taiwanese population (Hsiao et al, Ophthalmology (2012) 119: 522-527). According to data from Ocular TRUST (Tracking Resistance in the U.S. Today, Asbell, et al., 2008), more than 75% of MRSA were considered resistant to various fluoroquinolones such as ciprofloxacin, levofloxacin, gatifloxacin, and moxifloxacin. They have also shown to be resistant to other common antibiotics such as penicillin and tobramycin. Even with the arrival of newer antibiotics such as linezolid, daptomycin, and tigecyline, resistant bacteria still persist. Therefore, there is an urgent need for the development of new antibiotics that could combat these resistant bacteria.

The use of $\epsilon$-polylysine in contact lens care solutions has been described (see e.g. U.S. Pat. No. 6,187,264, and U.S. Pat. Publ. No. 2005/0074467). Another background application includes co-pending U.S. patent application Ser. No. 14/109,976. This reference and all references are incorporated in their entirety by reference herein.

SUMMARY

A feature of the present invention is to provide an ophthalmic composition that can be more effective in the treatment of an ocular infection and/or the source of the ocular infection.

A further feature of the present invention is to provide an ophthalmic composition that can provide an easy and non-toxic way to treat an ocular infection and/or the source of the ocular infection.

To achieve these and other advantages, and in accordance with the purposes of the present invention, as embodied and broadly described herein, the present invention relates to an ophthalmic composition for administration to an eye of a patient for the treatment or prophylaxis of an ocular infection, and/or the source of the ocular infection. The composition can comprise an amount of $\epsilon$-polylysine ($\epsilon$PL) effective for the treatment or prophylaxis of the ocular infection, and/or the source of the ocular infection. The ocular infection can be bacterial conjunctivitis. The ocular infection can be bacterial keratitis. The ocular infection can be bacterial endothalmitis. The ocular infection can be caused by a methicillin-resistant *Staphylococus aureus* (MRSA). The amount of $\epsilon$PL in the composition can be from about 0.001 and to about 2.0 percent by weight, based on the weight of the composition.

The present invention further relates to a method for the treatment or prophylaxis of an ocular infection of a patient. The method can comprise topically administering of an ophthalmic composition to the patient's eye. The ophthalmic composition comprises an effective amount of $\epsilon$-polylysine ($\epsilon$PL). The patient can be a human or a veterinary patient.

The present invention also relates to the use of an ophthalmic composition comprising a pharmaceutically acceptable carrier and an effective amount of $\epsilon$-polylysine ($\epsilon$PL) for the preparation of a medicament for topical administration to an eye of a patient for the treatment or prophylaxis of an ocular infection. The ocular infection can be caused by MRSA.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

It is to be understood that both the foregoing general description and the following detailed description are exemplary and explanatory only and intended to provide a further explanation of the present invention, as claimed.

DETAILED DESCRIPTION

The invention described herein is based on the discovery that $\epsilon$-polylysine ($\epsilon$PL) is highly effective against ocular pathogens, including methicillin-resistant *Staphylococus aureus* (MRSA), and is non-cytotoxic to ocular tissue when administered as an ophthalmic composition directly to an eye. Accordingly, provided herein is an ophthalmic composition for administration to an eye of a patient for the treatment or prophylaxis of an ocular infection, said composition comprising an amount of $\epsilon$-polylysine ($\epsilon$PL) effective for said treatment or prophylaxis and a pharmaceutically-acceptable carrier. In one example, the ocular infection is microbial keratitis, particularly bacterial keratitis. In another example, the ocular infection is microbial conjunctivitis, particularly bacterial conjunctivitis. In a specific example, the ocular infection is caused by *Staphylococus aureus*. In a further specific example, the ocular infection is caused by MRSA. In a specific example the ocular infection is bacterial endothalmitis. Bacterial endothalmitis is an infection of ocular cavities such as aqueous humor and/or vitreous humor caused by gram positive bacteria. It is a severe adverse event of cataract surgery. While the incidence is low, it can lead to blindness. Thus, the ophthalmic composition disclosed herein may be administered prophylactically to a patient before cataract surgery to prevent the development of bacterial endothalmitis. In one example, the patient is a mammal. In specific examples, the patient is a human patient or a veterinary patient.

As used herein, the term "ophthalmic composition" means a biocompatible and biodegradable composition. As used herein, the term "biodegradable" means that the ophthalmic composition eventually fully absorbs into the ocular tissue (including by lacrimal drainage). Thus, the term excludes medical devices such as contact lenses or intraocular lenses made from non-absorbable materials that may have εPL incorporated therein. In other words, the ophthalmic composition described herein consists of, or consists essentially of, εPL, a pharmaceutically acceptable carrier, and optionally one or more additional active agents and/or non-active agents such as lubricants, buffers, excipients, surfactants, and/or other agents that may conventional be found in eye drop solutions, gels, or creams. The term biocompatible means that the ophthalmic composition does not have undue toxicity or cause any physiological or pharmacological harmful effects. However, initial stinging or minor discomfort is common with topical ophthalmic formulations, and such minor reactions are not considered to render the ophthalmic compositions disclosed herein non-biocompatible.

εPL is commercially available as a homopolymer of L-lysine, ranging from about 25 to about 35 lysine (LYS) residues (see e.g CAS no. 28211-04-3). The εPL included in the ophthalmic composition of the present disclosure may include all fractions of the naturally-occurring εPL homopolymer. Alternatively, the εPLL may consist of a select fraction of εPL homopolymer. For example, the εPL may consist of homopolymers of εPL having at least 27 LYS residues, with lower molecular weight εPL homopolymers excluded from the ophthalmic composition. As an alternative to naturally-occurring εPL, the εPL used in the ophthalmic composition may be obtained from synthetic peptide methods. As used herein, the term εPL also includes derivatives of εPL provided that the derivatized form of the homopolymer retains antimicrobial activity. For example a derivatized εPL may be covalently attached to another polymer that increases residence time on the ocular tissue. In an alternative example, the εPL is underivatized, i.e. it consists of a homopolymer of L-lysine.

The amount of εPL in the ophthalmic composition is effective for the treatment or prophylaxis of the ocular infection and/or a source of the ocular infection. In a specific example the amount of εPL in the ophthalmic composition is effective for the treatment of the ocular infection. As used herein, "treatment" means the reduction of the infection or symptoms associated with the infection, or both. In another example, the amount of εPL in the ophthalmic composition is effective for the prophylaxis of the ocular infection. As used herein, "prophylaxis" means that an inoculum of an ocular pathogen introduced to an eye does not develop into a symptomatic ocular infection when the eye is dosed with the ophthalmic composition (either before or after introduction of the inoculum), whereas an eye not dosed with the ophthalmic composition (or treated with a control composition that lacks the εPL but is otherwise identical) develops a symptomatic ocular infection. Prophylaxis may be, for example, prophylaxis from infection following surgery, prophylaxis from infection after birth for the newborn, or prophylaxis from accidental contact with contaminating material. Routine clinical trials are conducted to establish dosages and administration regimens that are efficacious for the treatment and/or prophylaxis of the ocular infection, as guided by the pre-clinical in vitro and in vivo studies described in the Examples section below. Typically, the amount of εPL in the composition is at least 0.001% by weight (wt. %), 0.005 wt. %, 0.01 wt. %, 0.05 wt. %, or 0.1 wt. % up to 0.25 wt. %, 0.50 wt. %, 1.0 wt. %, 5.0 wt. %, or 10 wt. %, where wt. % of the εPL is calculated as a percentage of the weight of the composition. Throughout this disclosure, when a series of lower limit ranges and a series of upper limit ranges are provided, all combinations of the provided ranges are contemplated as if each combination were specifically listed. For example, in the above listing of εPL amounts, all 25 possible amount ranges are contemplated (i.e. 0.001-0.25 wt. %, 0.001-0.50 wt. 0% . . . 0.1-5 wt. %, and 0.1-10 wt. %. In a specific example the amount of εPL in the composition is from 0.001 to 1.0 percent by weight.

The ophthalmic composition may be formulated in any manner suitable for topical administration to an eye of a patient. Numerous suitable topical ophthalmic drug forms are well-known (see, e.g. Baranowski et al., The Scientific World Journal, Vol. 2014, Article ID 861904, incorporated herein by reference). In various examples, the ophthalmic composition is in the form of a solution, a suspension, an emulsion, an ointment, a cream, a gel, or a sustained release vehicle, such as an ocular insert. As used herein, "topical administration" includes administration of the ophthalmic composition to the surface of the cornea and/or to the surface of the conjunctiva. Topical administration also includes placement of the ophthalmic composition in the cul de sac of the eye. The ophthalmic composition may be aqueous or non-aqueous (e.g. mineral oil-based), but will generally be aqueous.

In one example, the ophthalmic composition is a sterile liquid, such as a solution or suspension, contained within a multi-use or single-use eye drop dispensing bottle or vial. In a specific example, the ophthalmic composition is provided as a sterile liquid comprising from about 0.005 to about 2.0 wt. % εPL contained within a multi-use eye drop dispensing bottle or vial. Typically the eye drop formulation comprises an aqueous buffered saline solution such as phosphate or borate buffered saline from about pH 4 to about 8, typically from about pH 7.0 to about 8.0, and more typically from about pH 7.2 to about pH 7.4. The osmolality of the formulation is typically in the range of about 200, 250, or 270 mOsm/kg up to about 310, 350, or 400 mOsm/kg. A liquid formulation packaged in a multi-use eye drop dispensing bottle may contain an added preservative, such as benzalkonium chloride. However, in some examples, the ophthalmic composition may be preservative-free. As used herein, "preservative-free" means that the composition comprises no preservative agent in addition to the εPL.

The composition, especially when formulated as a liquid, such as a solution or a suspension for dispensing by eye dropper, may contain an excipient that extends the period of time that a dose of the composition remains in contact with the cornea. For example, the excipient may be a viscosity-increasing agent and/or a mucoadhesive agent. Examples of such excipients include high molecular weight hydrophilic polymers including, but not limited to, polyvinyl alcohol, polyethylene glycol, carbomers, polycarbophil, polyoxyethylene-polyoxypropylene block copolymers (e.g. Poloxamer 407), cellulose derivatives (e.g. hydroxypropyl cellulose, hydroxypropyl methyl cellulose, carboxymethyl cellulose, and hydroxyethyl cellulose), natural polysaccharides (e.g. hyaluronic acid, dextran, chondroitin sulfate, gellan gum, xanthan gum, guar gum, trehalose, and tamarind seed polysaccharide). Additional mucoadhesive polymers are described in the literature (see e.g. Yadav et al. J. Chem. Pharm. Res., 2010, 2(5):418-432, incorporated herein by reference). Any combination of two or more of the foregoing polymers may be included in composition. As used herein, a high molecular weight polymer has a molecular weight of at least 100,000 daltons. In another example, the composition comprises a cyclodextrin (e.g. 2-hydroxypropyl-beta-cyclodextrin). In one example, the composition is formulated as a sustained release liquid. For example, the composition may be in the form of an ophthalmic suspension comprising mucoadhesive microspheres which sustain release of the ϵPL. The microspheres comprise a mucoadhesive polymer and ϵPL. Methods of making mucoadhesive microspheres for ophthalmic suspensions are described in the literature (see e.g. Dandagi et al., Sci Pharm (2013) 81(1):259-280).

In another specific example, the ophthalmic composition is formulated as unit dose ocular insert for placement in the eye's cul de sac. Methods of making ocular inserts are described in the literature (see e.g. U.S. Pat. No. 4,730,013, U.S. Pat. No. 7,749,970, and U.S. Pat Publ 2012/0215184, which are incorporated herein by reference). An ocular insert is a solid unit dosage form comprising of a biodegradable matrix containing the active agent, which in the case of the present ophthalmic compositions, is ϵPL. The matrix is typically made from a high molecular weight polymer or a combination of high molecular weight polymers, such as the aforementioned hydrophilic polymers and additional polymers disclosed in the aforementioned patent publications that describe ocular inserts. The ocular insert may additionally comprise a lubricant to enhance comfort. Upon placement in the eye, the ocular insert dissolves or erodes over a period of several hours to a day, and in some cases over several days.

Another aspect of the invention is a method of treating an ocular infection of a patient. The method comprises topically administering an ophthalmic composition comprising an effective amount of ϵ-polylysine (ϵPL) to the patient's eye. In various specific examples the patient is a human or a veterinary patient, and/or the ocular infection is bacterial conjunctivitis or bacterial keratitis, and/or the ocular infection is caused by MRSA.

The following Examples illustrate certain aspects and advantages of the present invention, which should be understood not to be limited thereby.

Example 1: Susceptibility Study

The $MIC_{50}$ and $MIC_{90}$ of ϵPL against methicillin-sensitive *Staphylococus aureus*) and MRSA were determined in these studies. (The "Minimum", "Maximum", and $MIC_{50}$ and $MIC_{90}$ in the Table are provided in units of µg/ml.) Other antimicrobial agents such as tobramycin, moxifloxacin, and PHMB (polyhexamethylene biguanid) were included for comparison. Broth microdilution tests were performed in accordance with the Clinical and Laboratory Standards Institute (CLSI) (M07-A9, Vol. 32 No. 2, January, 2012) for aerobic and facultative anaerobic strains. Cation-adjusted Mueller-Hinton broth was used for testing staphylococci species. The results, which are summarized in Table 1, demonstrate that both MSSA and MRSA are equally susceptible to ϵPL. The MICs were in a tight range, between 4 to 8 µg/ml, which suggests that no resistant isolates with much higher MICs were present in the 50 isolates tested.

TABLE 1

| Species | N | Active Agent | Minimum | Maximum | $MIC_{50}$ | $MIC_{90}$ |
|---|---|---|---|---|---|---|
| methicillin- | 25 | ϵPL | 4 | 8 | 8 | 8 |
| susceptible | 25 | Moxifloxacin | 0.03 | 1 | 0.06 | 1 |
| *S. aureus* | 25 | PHMB | 1 | 2 | 2 | 2 |
| (MSSA) | 25 | Tobramycin | 0.12 | 1 | 0.25 | 1 |
| methicillin- | 25 | ϵPL | 4 | 8 | 4 | 8 |
| resistant | 25 | Moxifloxacin | 0.03 | 8 | 1 | 4 |
| *S. aureus* | 25 | PHMB | 1 | 4 | 2 | 2 |
| (MRSA) | 25 | Tobramycin | 0.12 | 64 | 0.5 | 64 |

Example 2: Time-Kill Study

The bactericidal activity of ϵPL against MRSA strain K-950 was evaluated. The MIC of the tested strain was found to be 4.0 µg/mL ϵPL. Test tubes containing 0.5 mL of ϵPL at 0.25 µg/mL, 1.0 µg/mL, 4.0 µg/mL or 16.0 µg/mL ϵPL in Mueller Hinton broth growth media and approximately $10^6$ CFU/mL of K-950 were incubated at 37° C. After 1, 2, 4, 6, 8 and 24 hours of incubation, the test tubes were removed and colony forming units were calculated. To calculate CFU, 100 µL of the medium was removed from a tube and serially diluted (1:10 dilutions) in the medium. Aliquots of 100 µL of each dilution were plated, in duplicate, onto TSA agar plates containing 5% sheep's blood. The plates were incubated at 37° C. overnight and the colonies were counted the next day. The results, which are summarized in Table 2 below, indicate that ϵPL at 4 times the MIC concentration (16.0 µg/ml) decreased the MRSA colony counts by more than 3 logs at 8 hours post-inoculation while at MIC, it only caused a 2.4 Log decrease. At one quarter the MIC (1 µg/ml), it had no effect on the colony counts. The results of this study confirm that ϵPL is effective against MRSA and its action is bactericidal.

TABLE 2

| | Colony Counts CFU/ml | | | | | |
|---|---|---|---|---|---|---|
| | Time | | | | | |
| Group | 0 Hours | 1 Hour | 2 Hours | 4 Hours | 6 Hours | 8 Hours | 24 Hours |
| I - EPL 0.25X MIC (1 µg/ml) | $4.65 \times 10^5$ | $3.90 \times 10^5$ | $9.75 \times 10^5$ | $2.95 \times 10^7$ | $5.90 \times 10^6$ | $1.19 \times 10^7$ | $1.19 \times 10^8$ |
| II - EPL 1X MIC (4 µg/ml) | $3.75 \times 10^5$ | $4.70 \times 10^5$ | $3.90 \times 10^5$ | $6.30 \times 10^4$ | $5.60 \times 10^3$ | $1.50 \times 10^3$ | $1.56 \times 10^5$ |
| III - EPL 4X MIC (16 µg/ml) | $4.55 \times 10^5$ | $4.25 \times 10^5$ | $8.45 \times 10^4$ | $1.92 \times 10^3$ | $2.10 \times 10^2$ | $3.00 \times 10^1$ | $7.10 \times 10^3$ |
| VI - Growth Medium Only | $5.10 \times 10^5$ | $7.60 \times 10^5$ | $1.78 \times 10^6$ | $1.27 \times 10^7$ | $5.35 \times 10^7$ | $8.40 \times 10^7$ | $1.00 \times 10^8$ |

Example 3: Ocular Toxicity Study in Rabbits

Rabbits were divided into three treatment groups, each was treated with increasing concentrations of ∈PL (50, 150, and 500 μg/mL) in phosphate buffered saline (PBS) at pH 7.3. Specifically, rabbits from each group were dosed with a drop of ∈PL solution in the left eye of a rabbit eight times during a seven-hour period. The right eye was dosed with PBS. Macroscopic examinations were performed prior to the first dose, and 10 minutes following each dose. Slit lamp microscopic examinations were performed prior to the first dose and at termination. Ocular tissues were collected at termination and submitted for histological evaluation.

During the dosing period, there were some sporadic occurrences of conjunctival discharge as observed by macroscopic examination. However, they were equally divided between ∈ePL-treated and PBS-treated eyes. In addition, there was no dose-related relationship, indicating that the discharge is incidental. Both slit lamp microscopic examination and histologic findings did not reveal any abnormality that can be attributed to ∈PL treatment. Based on these findings, it was concluded that ocular application of ∈PL eight times during a seven-hour period with concentrations up to 500 μg/mL was well tolerated in rabbits.

Although the disclosure herein refers to certain illustrated examples, it is to be understood that these examples are presented by way of example and not by way of limitation. The intent of the foregoing detailed description, although discussing exemplary examples, is to be construed to cover all modifications, alternatives, and equivalents of the examples as may fall within the spirit and scope of the invention as defined by the additional disclosure.

The present invention includes the following aspects/embodiments/features in any order and/or in any combination:

1. An ophthalmic composition for administration to an eye of a patient for the treatment or prophylaxis of an ocular infection, said composition comprising an amount of ∈-polylysine (∈PL) effective for said treatment.
2. The composition of any preceding or following embodiment/feature/aspect, wherein the ocular infection is bacterial conjunctivitis.
3. The composition of any preceding or following embodiment/feature/aspect, wherein the ocular infection is bacterial keratitis.
4. The composition of any preceding or following embodiment/feature/aspect, wherein the ocular infection is bacterial endothalmitis.
5. The composition of any preceding or following embodiment/feature/aspect, wherein the ocular infection is bacterial endothalmitis.
6. The composition of any preceding or following embodiment/feature/aspect, wherein the ocular infection is caused by a methicillin-resistant *Staphylococus aureus* (MRSA).
7. The composition of any preceding or following embodiment/feature/aspect, wherein the amount of ∈PL is between 0.001 and 2.0 percent by weight.
8. The composition of any preceding or following embodiment/feature/aspect, further comprising a viscosity-increasing agent.
9. The composition of any preceding or following embodiment/feature/aspect, further comprising a mucoadhesive agent.
10. The composition of any preceding or following embodiment/feature/aspect, further comprising an excipient that is a polyvinyl alcohol, polypropylene glycol, a carbomer, polycarbophil, a polyoxyethlene-polyoxypropylene block copolymer, hydroxypropyl cellulose, hydroxypropyl methyl cellulose, carboxymethyl cellulose, hydroxyethyl cellulose, hyaluronic acid, dextran, chondroitin sulfate, gellan gum, xanthan gum, guar gum, trehalose, tamarind seed polysaccharide, or a cyclodextrin, or any combinations of any two or more of the foregoing excipients.
11. The composition of any preceding or following embodiment/feature/aspect, wherein the composition is preservative-free.
12. The composition of any preceding or following embodiment/feature/aspect, wherein the composition is formulated as a liquid for administering by one or more drops to the eye.
13. The composition of any preceding or following embodiment/feature/aspect, wherein the composition is formulated as a unit dose ocular insert for placement in the eye's cul de sac.
14. An eye drop dispensing bottle comprising in liquid form, the ophthalmic composition of any preceding or following embodiment/feature/aspect.
15. A method for the treatment or prophylaxis of an ocular infection of a patient, said method comprising topically administering of an ophthalmic composition comprising an effective amount of ∈-polylysine (∈PL) to the patient's eye.
16. The method of any preceding or following embodiment/feature/aspect, wherein the patient is a human or a veterinary patient.
17. The method of any preceding or following embodiment/feature/aspect, wherein the method is for the treatment of bacterial conjunctivitis.
18. The method of any preceding or following embodiment/feature/aspect, wherein the method is for the treatment of bacterial keratitis.
19. The method of any preceding or following embodiment/feature/aspect, wherein the ocular infection is caused by MRSA.
20. The method of any preceding or following embodiment/feature/aspect, wherein the ophthalmic composition is administered to the patient prior to cataract surgery for prophylaxis against bacterial endothalmitis.
21. Use of an ophthalmic composition comprising a pharmaceutically acceptable carrier and an effective amount of ∈-polylysine (∈PL) for the preparation of a medicament for topical administration to an eye of a patient for the treatment or prophylaxis of an ocular infection.
22. The use of any preceding or following embodiment/feature/aspect, wherein the ocular infection is caused by MRSA.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An ophthalmic composition for use in the treatment of an ocular infection when the ophthalmic composition is administered to an eye of a patient, or the prophylaxis of an ocular infection when the ophthalmic composition is administered to an eye of a patient before or after the introduction of an inoculum of an ocular pathogen, said composition consisting essentially of a pharmaceutically-acceptable carrier, an amount of ϵ-polylysine (ϵPL) effective for said treatment, and optionally at least one non-active agent, wherein the ophthalmic composition is provided as a liquid in an eye-drop dispensing bottle or vial, or as a unit dose ocular insert for placement in a cul de sac of the patient's eye, wherein the composition comprises no preservative agent in addition to the ϵ-polylysine (ϵPL).

2. The composition for use of claim 1, wherein the ocular infection is bacterial conjunctivitis.

3. The composition for use of claim 1, wherein the ocular infection is bacterial keratitis.

4. The composition for use of claim 1, wherein the ocular infection is bacterial endophthalmitis.

5. The composition for use of claim 1, wherein the ocular infection is caused by a methicillin-resistant *Staphylococus aureus* (MRSA).

6. The composition for use of claim 1, wherein the amount of ϵPL is between 0.001 and 2.0 percent by weight.

7. The composition for use of claim 1 wherein said non-active agent is present and is a viscosity-increasing agent.

8. The composition for use of claim 1 wherein said non-active agent is present and is a mucoadhesive agent.

9. The composition for use of claim 1 wherein said non-active agent is present and is an excipient that is a polyvinyl alcohol, polypropylene glycol, a carbomer, polycarbophil, a polyoxyethylene-polyoxypropylene block copolymer, hydroxypropyl cellulose, hydroxypropyl methyl cellulose, carboxymethyl cellulose, hydroxyethyl cellulose, hyaluronic acid, dextran, chondroitin sulfate, gellan gum, xanthan gum, guar gum, trehalose, tamarind seed polysaccharide, or a cyclodextrin, or any combinations of any two or more of the foregoing excipients.

10. The composition for use of claim 1, wherein the composition is formulated as said liquid for administering by one or more drops to the eye.

11. The composition for use of claim 1, wherein the composition is formulated as said unit dose ocular insert for placement in the eye's cul de sac.

12. An eye drop dispensing bottle comprising in liquid form, the ophthalmic composition for use in the treatment of or prophylaxis of an ocular infection of claim 1.

13. A method for the treatment of an ocular infection of a patient, said method comprising topically administering of an ophthalmic composition consisting essentially of a pharmaceutically-acceptable carrier, an effective amount of ϵ-polylysine (ϵPL), and optionally at least one non-active agent, to the patient's eye, wherein the ophthalmic composition is administered as a liquid from an eye-drop dispensing bottle or vial, or as a unit dose ocular insert placed in a cul de sac of the patient's eye, and wherein the composition comprises no preservative agent in addition to the ϵ-polylysine (ϵPL), or a method for the prophylaxis of an ocular infection of a patient, said method comprising topically administering of an ophthalmic composition consisting essentially of a pharmaceutically-acceptable carrier, an effective amount of ϵ-polylysine (ϵPL), and optionally at least one non-active agent, to the patient's eye before or after the introduction of an inoculum of an ocular pathogen, wherein the ophthalmic composition is administered as a liquid from an eye-drop dispensing bottle or vial, or as a unit dose ocular insert placed in a cul de sac of the patient's eye, and wherein the composition comprises no preservative agent in addition to the ϵ-polylysine (ϵPL).

14. The method of claim 13, wherein the patient is a human or a veterinary patient.

15. The method of claim 13, wherein the method is for the treatment of bacterial conjunctivitis.

16. The method of claim 13, wherein the method is for the treatment of bacterial keratitis.

17. The method of claim 13, wherein the ocular infection is caused by MRSA.

18. The method of claim 13, wherein the ophthalmic composition is administered to the patient prior to cataract surgery for prophylaxis against bacterial endophthalmitis.

* * * * *